(12) United States Patent
Qian

(10) Patent No.: US 10,642,155 B2
(45) Date of Patent: May 5, 2020

(54) MIXED-TYPE PHOTOSENSITIVE RESIN AND PREPARATION METHOD THEREFOR

(71) Applicants: Changzhou Tronly Advanced Electronic Materials Co., Ltd., Changzhou (CN); Changzhou Tronly New Electronic Materials Co., Ltd., Changzhou (CN)

(72) Inventor: Xiaochun Qian, Changzhou (CN)

(73) Assignees: Changzhou Tronly Advanced Electronic Materials Co., Ltd., Changzhou (CN); Changzhou Tronly New Electronic Materials Co., Ltd., Changzhou (CN)

( * ) Notice: Subject to any disclaimer, the term of this patent is extended or adjusted under 35 U.S.C. 154(b) by 0 days.

(21) Appl. No.: 16/246,379

(22) Filed: Jan. 11, 2019

(65) Prior Publication Data

US 2019/0391491 A1    Dec. 26, 2019

Related U.S. Application Data

(63) Continuation of application No. PCT/CN2017/092228, filed on Jul. 7, 2017.

(30) Foreign Application Priority Data

Jul. 13, 2016   (CN) .......................... 2016 1 0550205

(51) Int. Cl.
| | | |
|---|---|---|
| *G03F 7/029* | (2006.01) | |
| *C09D 133/14* | (2006.01) | |
| *C07D 305/06* | (2006.01) | |
| *C08F 20/68* | (2006.01) | |
| *C08F 22/20* | (2006.01) | |
| *C09D 135/02* | (2006.01) | |

(52) U.S. Cl.
CPC ........... *G03F 7/029* (2013.01); *C07D 305/06* (2013.01); *C08F 20/68* (2013.01); *C08F 22/20* (2013.01); *C09D 133/14* (2013.01); *C09D 135/02* (2013.01)

(58) Field of Classification Search
CPC ........ C07D 305/06; C08F 20/68; C08F 22/20; C09D 133/14; C09D 135/02
USPC ....................................................... 549/510
See application file for complete search history.

(56) References Cited

U.S. PATENT DOCUMENTS

| | | |
|---|---|---|
| 2,895,931 A | 7/1959 | Klug |
| 3,111,470 A | 11/1963 | Marans |
| 3,209,013 A | 9/1965 | Hechenbleikner et al. |
| 3,341,475 A | 9/1967 | Vandenberg |
| 4,946,992 A | 8/1990 | Falk et al. |
| 5,663,289 A | 9/1997 | Archibald et al. |
| 6,084,004 A | 7/2000 | Weinmann et al. |
| 6,284,898 B1 | 9/2001 | Moszner et al. |
| 6,495,636 B2 | 12/2002 | Sugiyama et al. |
| 6,586,496 B1 | 7/2003 | Takamatsu et al. |
| 6,770,737 B2 | 8/2004 | Kakuchi et al. |
| 7,423,097 B2 | 9/2008 | Inata |
| 7,524,610 B2 | 4/2009 | Kim et al. |
| 7,534,820 B2 | 5/2009 | Kohno et al. |
| 7,902,305 B2 | 3/2011 | Kong |
| 8,883,942 B2 | 11/2014 | Frank et al. |
| 9,249,126 B2 | 2/2016 | Kim et al. |
| 9,575,409 B2 | 2/2017 | Ng et al. |
| 9,822,088 B2 | 11/2017 | Wohl et al. |
| 2003/0017341 A1 | 1/2003 | Gross et al. |
| 2003/0158286 A1 | 8/2003 | Nishizaki et al. |
| 2005/0061429 A1 | 3/2005 | Hosaka |
| 2005/0288386 A1 | 12/2005 | Ishikawa |
| 2006/0025542 A1 | 2/2006 | Musa |
| 2007/0164255 A1 | 3/2007 | Seki et al. |
| 2008/0081133 A1* | 4/2008 | Kato ....................... C08F 26/06 428/1.1 |
| 2011/0052831 A1 | 3/2011 | Kyota |
| 2011/0190418 A1 | 8/2011 | Noguchi et al. |
| 2012/0309930 A1 | 12/2012 | Araki et al. |
| 2013/0035465 A1 | 2/2013 | Araki et al. |
| 2014/0093699 A1 | 4/2014 | Xu |
| 2014/0303274 A1 | 10/2014 | Liu et al. |
| 2016/0083505 A1 | 3/2016 | Tanaka |
| 2018/0237579 A1 | 8/2018 | Fujikawa et al. |
| 2019/0144405 A1* | 5/2019 | Qian ................... C07D 407/12 549/510 |

FOREIGN PATENT DOCUMENTS

| | | |
|---|---|---|
| CN | 101035856 A | 9/2007 |
| CN | 101776846 A | 7/2010 |
| CN | 102753588 A | 10/2012 |
| CN | 102782072 A | 11/2012 |
| CN | 102834431 A | 12/2012 |
| CN | 104447635 A | 3/2015 |
| CN | 104745104 A | 7/2015 |
| CN | 104774312 A | 7/2015 |
| JP | 1132001081182 A | 3/2001 |
| JP | 1212009114337 A | 5/2009 |
| JP | 1232011062070 A | 3/2011 |
| JP | 1232011168561 A | 9/2011 |
| JP | H232011168561 A | 9/2011 |
| JP | 1242012241036 A | 12/2012 |
| WO | 2015085428 A1 | 6/2015 |
| WO | WO-2019019924 A1 * | 1/2019 |

OTHER PUBLICATIONS

Crivello; Journal of Polymer Science, Part A Polymer Chemistry, 2015, 53, 594-601. (Year: 2015).*

(Continued)

*Primary Examiner* — Daniel R Carcanague
(74) *Attorney, Agent, or Firm* — Cook Alex, Ltd.

(57) ABSTRACT

A hybrid photosensitive resin having a structure represented by general formula (I) and contains an oxetanyl functional group and a (meth)acryloxy functional group. The functional groups are coordinated with each other and the functionality is adjustable and controllable. The hybrid photosensitive resin is highly suitable for radical-cation photocuring systems, there is no problem of polymerization inhibition by oxygen, and its cured film has high hardness, good flexibility, excellent adherence, and excellent heat resistance.

12 Claims, No Drawings

(56) References Cited

OTHER PUBLICATIONS

Written Opinion of the International Searching Authority in application PCT/CN2017/092228, dated Sep. 12, 2017. English Translation. (Year: 2017).*
International Search Report and Written Opinion dated Sep. 12, 2017 in connection with International application No. PCT/CN2017/092228.
Wangfu et al., "Study on the Properties of Oxetane Acrylate Uv-Cured Hybrid System", Imaging Science and Photochemistry, (2014) pp. 289-299.
Deng et al., "Study on Its Uv—Curing Properties With a Novel Reactive Diluent in a Radical/Cationic Hybrid System", Speciality Petrochemicals, (2016) pp. 45-50.
First Office Action dated Apr. 24, 2019 in connection with Chinese application No. 201610550205.6.
First Office Action dated Nov. 19, 2019 in connection with Japanese application No. 2018-568217.

* cited by examiner

MIXED-TYPE PHOTOSENSITIVE RESIN AND PREPARATION METHOD THEREFOR

CROSS-REFERENCE TO RELATED APPLICATIONS

This application is a continuation of International Application No. PCT/CN2017/092228 having an international filing date of Jul. 7, 2017 entitled "Mixed-Type Photosensitive Resin and Preparation Method Therefor". The PCT/CN2017/092228 international application claimed priority benefits, in turn, from Chinese Patent Application No. 201610550205.6 filed on Jul. 13, 2016. The '228 international application is hereby incorporated by reference herein in its entirety.

FIELD OF THE INVENTION

This invention belongs to the field of organic chemistry, and particularly to a hybrid photosensitive resin and a preparation method thereof.

According to the mechanism of curing, initiation systems used in a radiation-curable technique mainly include two types: radical type curing systems and cation type curing systems. Radical type curing systems have high curing speeds and various types of initiators. There are deficiencies, which are difficult to overcome regarding radical type curing systems. For example, the volume shrinkage upon curing is relatively large, which severely affects the adherence of a coating layer to a substrate; the phenomenon of polymerization inhibition by oxygen is relatively severe and it is difficult to cure the surface of a thin coating layer; dead spots which cannot be irradiated by ultraviolet light cannot be cured, and so on. With respect to the cation type curing system, the volume shrinkage after curing is small, the adhesion is strong, and there is no problem of polymerization inhibition by oxygen in the process curing. A relatively dark part or a part which cannot be irradiated by ultraviolet light can be effectively and completely cured by post curing. The disadvantages include low curing speed, low production efficiency, and fewer types of suitable initiators.

In recent years, with respect to different characteristics of the radical type initiation system and the cation type initiation system, there has been a radical-cation hybrid polymerization system, which can effectively combine advantages of radical curing and cation curing to produce a cured product having good properties. However, types of prepolymers suitable for such a curing system are few and selectivities are limited, and it is difficult to achieve synchronous curing with respect to curing speeds of a radical photocurable resin and a cation photocurable resin in the system, thereby leading to bad hardness and adherence of products after curing.

Hybrid photosensitive resins are an important research trend for overcoming such deficiencies. There have been some reported patents about hybrid photosensitive resins. For example, JP2011168561A discloses a compound having a plurality of oxetanyl functional groups and acryloxy functional groups, which has a relatively high curing speed and a relatively high hardness. However, this compound has poor flexibility and adherence which is not good enough, which greatly affects properties of photosensitive materials.

SUMMARY OF THE INVENTION

A hybrid photosensitive resin contains an oxetanyl functional group and a (meth)acryloxy functional group and the functionality thereof is adjustable and controllable. In at least some embodiments, the hybrid photosensitive resin has good application properties. When used in radical cation curing systems, the curing speed is high, there is no, or at least little polymerization inhibition by oxygen, and its cured film has high hardness, good flexibility, excellent adherence, and excellent heat resistance.

In order to achieve the object described above, the hybrid photosensitive resin has a structure represented by general formula (I):

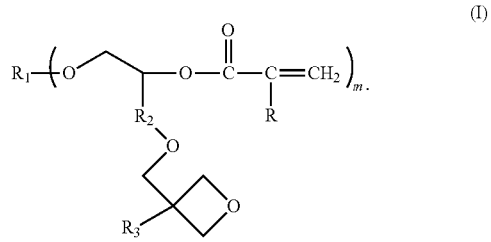

$R_1$ represents a $C_1$-$C_{40}$ linear-valent alkyl group, a $C_1$-$C_{40}$ branched m-valent alkyl group, a $C_2$-$C_{20}$ m-valent alkenyl group, or a $C_6$-$C_{40}$ m-valent aryl group, wherein —$CH_2$— can be substituted with an oxygen atom, —NH—, or a 1,4-phenylene group, provided that two —O—'s are not directly connected; and wherein, one or more hydrogen atoms in these groups can be each independently substituted with a group selected from an alkyl group, a halogen, and a nitro group; $R_2$ represents a $C_1$-$C_{20}$ linear alkylene group, $C_1$-$C_{20}$ branched alkylene group, wherein —$CH_2$— in the main chain can be substituted with an oxygen atom, provided that two —O—'s are not directly connected, and, one or more hydrogen atoms in the group can be each independently substituted with a group selected from an alkyl group, a halogen, and a nitro group; $R_3$ represents hydrogen, a halogen, a nitro group, a $C_1$-$C_{20}$ linear alkyl group, a $C_1$-$C_{20}$ branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_2$-$C_{10}$ alkenyl group, or a $C_6$-$C_{20}$ aryl group, and optionally, one or more hydrogen atoms in these groups can be each independently substituted with a group selected from an alkyl group, a halogen, and a nitro group; and R represents hydrogen or a methyl group; and m represents an integer of 1-8.

In the structure represented by general formula (I) described above, m oxetanyl functional groups and m (meth)acryloxy functional groups are connected by a m-valent linking group $R_1$ to form a whole.

In some preferred embodiments, $R_1$ represents a $C_1$-$C_{40}$ linear m-valent alkyl group, a $C_1$-$C_{40}$ branched m-valent alkyl group, a $C_2$-$C_{10}$ linear m-valent alkenyl group, a $C_2$-$C_{10}$ branched m-valent alkenyl group, or a $C_6$-$C_{30}$ m-valent aryl group, wherein —$CH_2$— can be substituted with an oxygen atom, —NH—, or a 1,4-phenylene group, provided that two —O—'s are not directly connected; and wherein, one or more hydrogen atoms in these groups can be each independently substituted with a group selected from an alkyl group, a halogen, and a nitro group.

In some embodiments, $R_1$ can be selected from the following structures: a $C_1$-$C_{12}$ linear 1-to-4-valent alkyl group, a $C_1$-$C_{12}$ branched 1-to-4-valent alkyl group,

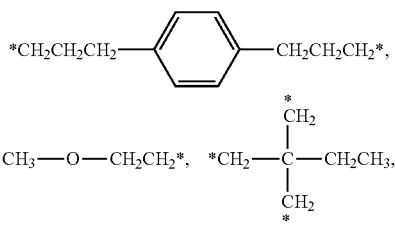

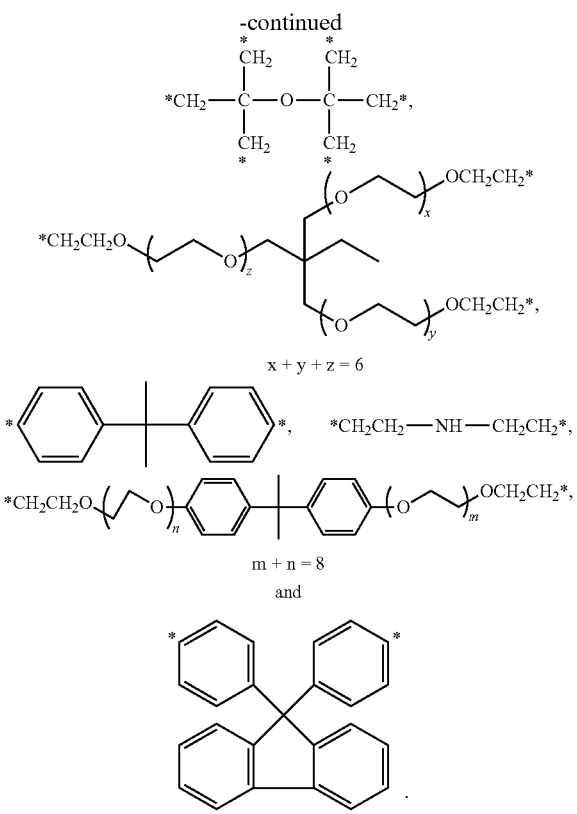

x + y + z = 6 m + n = 8 and

In at least some preferred embodiments, $R_2$ represents a $C_1$-$C_{10}$ linear alkylene group or a $C_1$-$C_{10}$ branched alkylene group, wherein —$CH_2$— in the main chain can be substituted with an oxygen atom, provided that two —O—'s are not directly connected.

In at least some preferred embodiments, $R_2$ represents a $C_1$-$C_6$ linear alkylene group or $C_1$-$C_6$ branched alkylene group, wherein —$CH_2$— in the main chain can be optionally substituted with an oxygen atom, provided that two —O—'s are not directly connected.

In at least some preferred embodiments, $R_3$ represents hydrogen, a $C_1$-$C_{10}$ linear alkyl group, a $C_1$-$C_{10}$ branched alkyl group, a $C_3$-$C_{10}$ cycloalkyl group, a $C_4$-$C_{10}$ cycloalkylalkyl group, a $C_4$-$C_{10}$ alkylcycloalkyl group, a $C_2$-$C_8$ alkenyl group, or a phenyl group. Further preferably, $R_3$ represents a $C_1$-$C_4$ linear alkyl group or a $C_1$-$C_4$ branched alkyl group, or a $C_4$-$C_8$ cycloalkylalkyl group. In at least some preferred embodiments, m is an integer of 1-6, more preferably an integer of 1-4.

Unless otherwise specified, related terms have the meanings as commonly understood in the art. A range of a numeric value includes endpoint values and all point values between the endpoint values. For example, "$C_1$-$C_{10}$" includes $C_1$, $C_2$, $C_3$, $C_4$, $C_5$, $C_6$, $C_7$, $C_8$, $C_9$, and $C_{10}$, and "an integer of 1-4" includes 1, 2, 3, and 4.

A preparation method of the hybrid photosensitive resin represented by general formula (I) described above, which uses a hydroxy-containing compound represented by general formula (II) and an oxetanyl-containing compound represented by general formula (III) as starting materials, and can comprise the steps of:

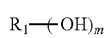 (II)

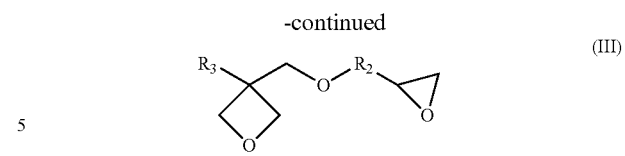 (III)

(1) ring opening reaction, wherein the compound of general formula (II) is reacted with the compound of general formula (III) in the presence of a catalyst to obtain an intermediate; and a reaction formula thereof is as follows:

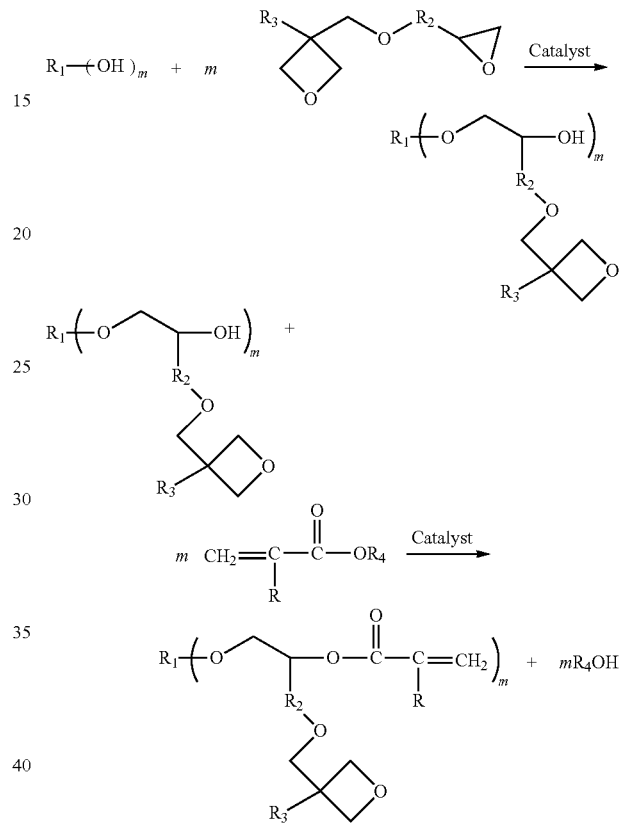

(2) esterification/transesterfication reaction, wherein the intermediate is reacted with (meth) acrylic acid or (meth) acrylate in the presence of a catalyst to obtain a product; wherein $R_4$ represents hydrogen or a $C_1$-$C_4$ alkyl group (e.g., $CH_3$, $CH_3CH_2$, $CH_3CH_2CH_2$, and the like).

The catalyst used in the reaction in step (1) can be: an alkali metal hydroxide, such as sodium hydroxide, potassium hydroxide, and the like; an alkali metal salt of an alcohol, such as sodium methoxide, potassium ethanoxide, sodium tert-butoxide, and the like; an alkali metal carbonate, such as sodium carbonate, potassium carbonate, and the like; an alkali metal bicarbonate, such as sodium bicarbonate, potassium bicarbonate, and the like; an alkyl metal lithium compound, such as butyl lithium, phenyl lithium, and the like; and a lithium amide compound, such as a lithium diisopropylamide, lithium hexamethyldisilylamide and the like. The usage amount of the catalyst can be easily determined. In some preferred embodiments, the usage amount of the catalyst is 0.1-20% of the molar amount of the compound of general formula (II), more preferably 1-20%.

According to the type of the raw material, the reaction system in step (1) can optionally comprise an organic solvent. The type of the solvent used suitably is not particularly limited, as long as it can dissolve reactive raw materials and does not negatively affect the reaction. For example, it can be: a nitrile solvent, such as acetonitrile, propionitrile, benzonitrile, and the like; an amide solvent, such as N,N-dimethylformamide, N,N-dimethylacetamide, N-methylpyrrolidone, and the like; an ether solvent, such as tetrahydrofuran, dioxane, and the like; and an aromatic solvent, such as benzene, toluene, xylene, and the like. These solvents can be used alone or can be used by mixing two or more thereof, and the total usage amount can be properly adjusted according to the uniformity and the stirring property of the reaction system. This can be easily determined.

In at least some embodiments, the temperature of the reaction in step (1) is typically 25-200° C., and preferably 50-150° C. The reaction pressure is not particularly limited, and is typically atmospheric pressure. After completion of the reaction, pH is adjusted to neutral, and filtration, water washing, extraction, and reduced-pressure distillation are performed to obtain an intermediate compound.

The intermediate compound is subjected to esterification reaction with (meth) acrylic acid or transesterfication reaction with (meth) acrylate in step (2) to obtain the compound of general formula (I).

The reaction of step (2) is performed in an organic solvent containing the catalyst. The type of the solvent is not particularly limited, as long as it can dissolve reactive raw materials and do not negatively affect the reaction, for example, an aromatic solvent, such as benzene, toluene, xylene, and the like. These solvents can be used alone or can be used by mixing two or more thereof, and the total usage amount can be properly adjusted according to the uniformity and the stirring property of the reaction system. This can be easily determined.

The catalyst used in the esterification reaction can be an inorganic acid, such as hydrochloric acid, phosphate, boric acid, concentrated sulfuric acid, and the like, or can be an organic acid, such as p-toluenesulfonic acid, methanesulfonic acid, and the like. The catalyst used in the transesterfication reaction can be a titanate-based compound, such as one or a combination of two or more of 2-ethylhexyl titanate, tetramethyl titanate, tetraethyl titanate, tetraisopropyl titanate, tetrabutyl titanate, tetraisobutyl titanate, and the like. The usage amount of the catalyst can be easily determined. In some preferred embodiments, the usage amount of the catalyst is 0.05-5 wt %, more preferably 0.1-2 wt % of the intermediate compound.

In at least some embodiments, the temperature of the reaction is typically 0-200° C., preferably 50-150° C. After completion of the reaction, water washing is performed to become neutral and the solvent is removed by reduced-pressure distillation to obtain a compound of interest.

In at least some embodiments, the disclosed hybrid photosensitive resin comprises a plurality of oxetanyl functional groups and (meth)acryloxy functional groups. By structure optimization, the functional groups are coordinated with each other. It results in a resin that is highly suitable for radical-cation photocuring systems, the curing speed is high, there is no problem of polymerization inhibition by oxygen, and its cured film has high hardness, good flexibility, excellent adherence, and excellent heat resistance.

DETAILED DESCRIPTION OF ILLUSTRATIVE EMBODIMENT(S)

It is to be indicated that Examples in this application and features in the Examples can be combined with each other without being conflicted.

This application will be further described in detail in conjunction with specific Examples below. These Examples should not be construed as limiting the scope sought to be protected this application.

PREPARATION EXAMPLE

Example 1

(1) Preparation of Intermediate 1a:

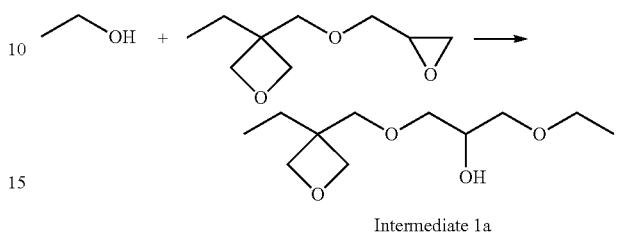

Intermediate 1a

In an example embodiment, 23 g of ethanol and 2 g of sodium hydroxide were added to a 250 ml four-neck flask mounted with a stirring apparatus, a thermometer, and a reflux condenser tube, and the temperature was increased to 50° C. with stirring. 86 g of 3-ethyl-3-[(oxiranylmethoxy)methyl]oxetane was dropped within 1 h, and reaction was continued with stirring. Vapor phase tracking was performed until the content of ethanol did not change, and heating was stopped. The pH was adjusted to neutral, and filtration, water washing, extraction, and reduced-pressure distillation were performed to obtain 103 g of the intermediate 1a.

(2) Preparation of Compound 1:

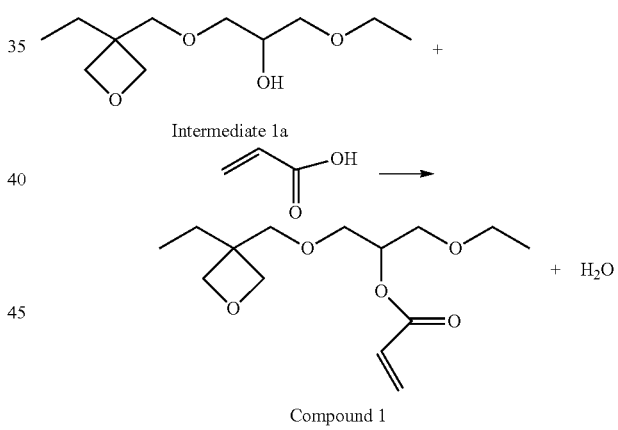

Compound 1

In an example embodiment, 100 g of the intermediate 1a, 33 g of acrylic acid, 0.2 g of p-toluenesulfonic acid, and 100 ml of toluene were added to a 250 ml four-neck flask mounted with a reflux condenser tube. Reaction was performed with heating reflux and tracked until no water was brought out, and the reaction was stopped. The temperature was decreased, water washing was performed to become neutral, and the solvent was removed by reduced-pressure distillation to obtain 120 g of the product of interest.

The structure of the compound 1 was confirmed by GC-MS and $^1$H-NMR.

MS (m/e): 272 (M)

$^1$H-NMR(CDCl$_3$, 500 MHz): $\delta$0.96 (3H, m), $\delta$1.13 (2H, m), $\delta$1.25 (2H, m), $\delta$3.29 (2H, s), $\delta$3.42 (2H, m), $\delta$3.61 (4H, d), $\delta$4.61 (1H, m), $\delta$4.66 (4H, s), $\delta$5.82-6.42 (3H, m).

Example 2

(1) Preparation of Intermediate 2a:

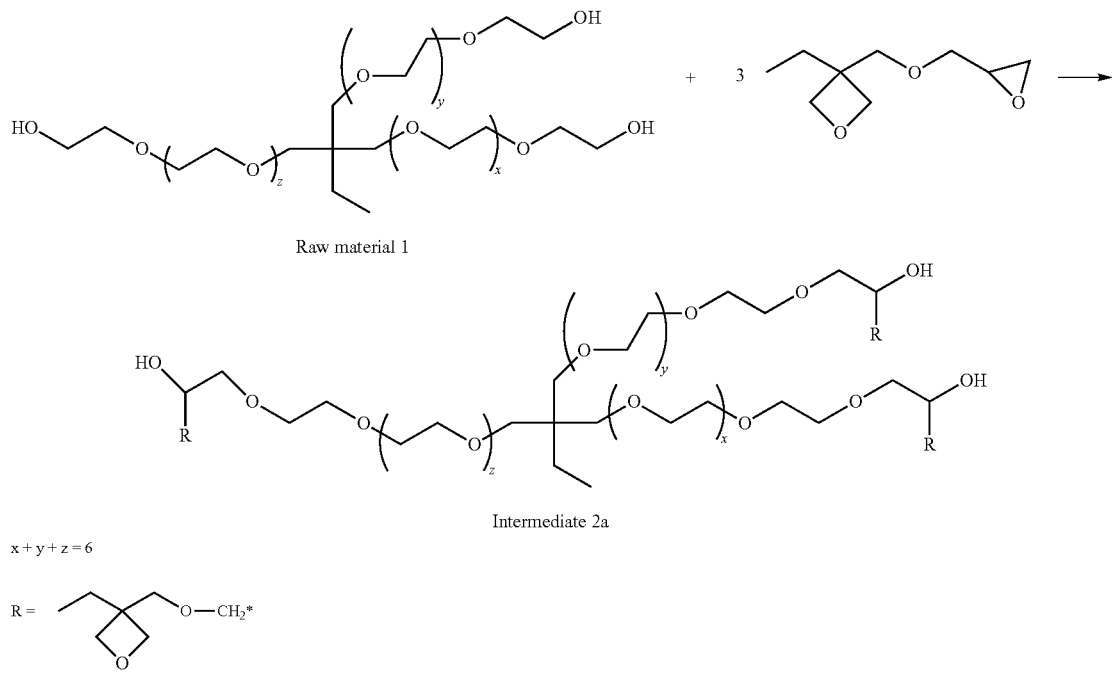

Raw material 1

Intermediate 2a $x + y + z = 6$

R =

In an example embodiment, 265 g of the raw material 1, 4 g of sodium hydroxide, and 300 ml of toluene were added to a 1000 ml four-neck flask mounted with a stirring apparatus, a thermometer, and a reflux condenser tube, and the temperature was increased to 80° C. with stirring. 258 g of 3-ethyl-3-[(oxiranylmethoxy) methyl]oxetane was dropped within 1.5 h, and reaction was continued with stirring. Vapor phase tracking was performed until the content of the raw material 1 did not change, and heating was stopped. The pH was adjusted to neutral, and filtration, water washing, extraction, and reduced-pressure distillation were performed to obtain 507 g of the intermediate 2a.

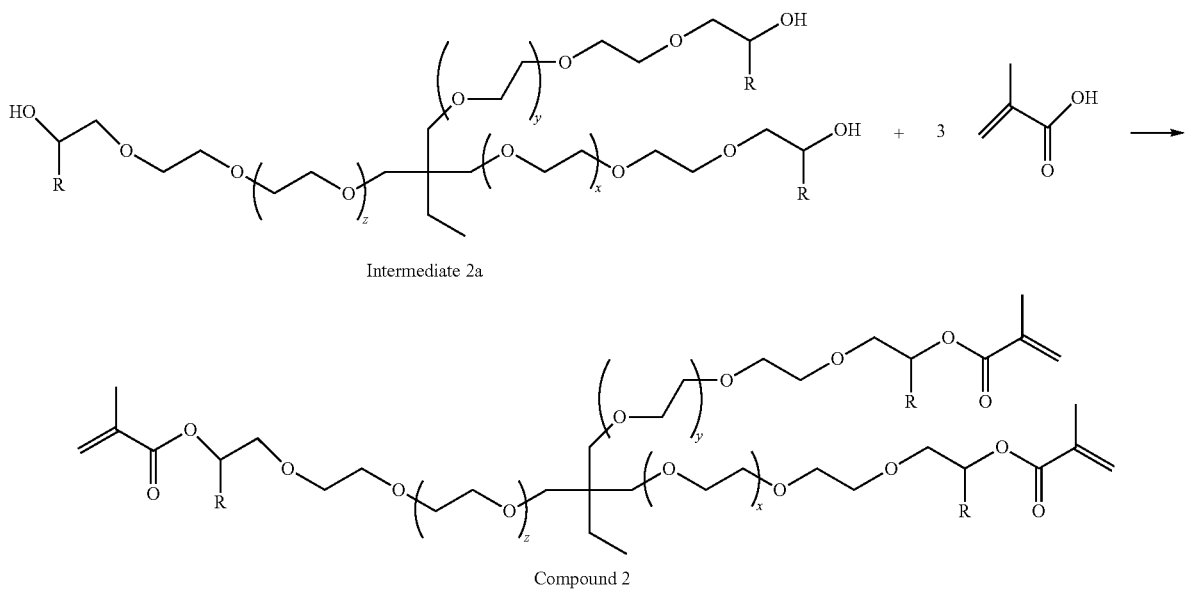

Intermediate 2a

Compound 2

$x + y + z = 6$

R =

(2) Preparation of Compound 2:

In an example embodiment, 100 g of the intermediate 2a, 24.7 g of methacrylic acid, 0.2 g of p-toluenesulfonic acid, and 130 ml of toluene were added to a four-neck flask mounted with a reflux condenser tube. The reaction was performed with heating reflux until no water was brought out, and the reaction was stopped. The temperature was decreased, water washing was performed to become neutral, and the solvent was removed by reduced-pressure distillation to obtain 116 g of the compound of interest.

The structure of the compound 2 was confirmed by GPC and IR.

GPC: $\overline{M}_w$=1250;
IR(KBr), v/cm$^{-1}$:

981(s, 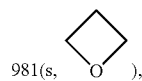), 1630 (s, C=C), 1200 (m, C—O—C), 1720 (s, C=O).

Example 3

Compound 3-11 having structures as shown in Table 1 were synthesized by using corresponding agents with reference to the methods of Examples 1 and 2.

TABLE 1

| Compound | Structure | $^1$H-NMR/IR(KBr) |
|---|---|---|
| 3 | 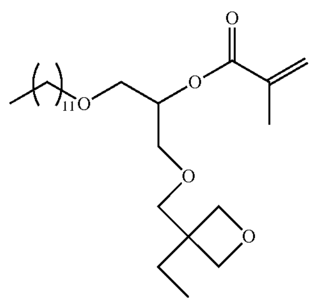 | δ0.96(6H, m)<br>δ1.25-1.93(25H, m)<br>δ3.29-3.61(8H, m)<br>δ4.61-4.65(5H, m)<br>δ5.58-6.15(2H, m) |
| 4 | 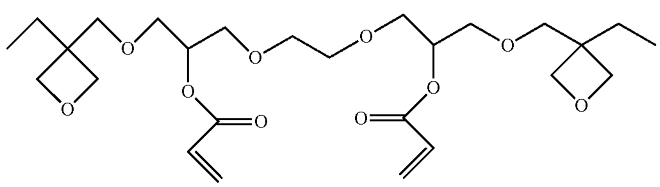 [SMILES: C=CC(=O)OC(COCCOCC(COCC1(CC)COC1)OC(=O)C=C)COCC1(CC)COC1] | δ0.96(6H, m)<br>δ1.25-1.93(6H, m)<br>δ3.29-3.61(16H, m)<br>δ4.61-6.51(14H, m) |
| 5 | | δ0.96(12H, m)<br>δ1.25(8H, m)<br>δ3.29-4.65(39H, m)<br>δ5.80-6.43(9H, m) |
| 6 | 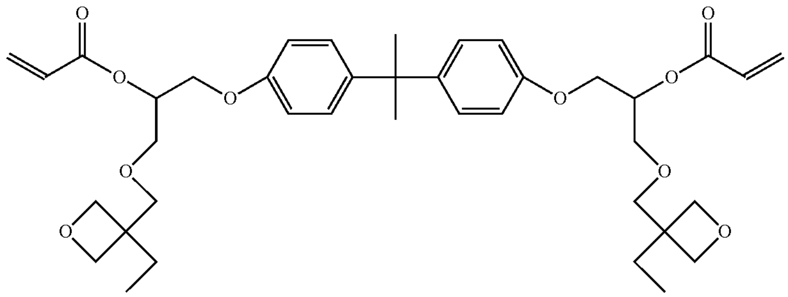 [SMILES: C=CC(=O)OC(COCC1(CC)COC1)COc1ccc(C(C)(C)c2ccc(OCC(COCC3(CC)COC3)OC(=O)C=C)cc2)cc1] | δ0.96(6H, m)<br>δ1.25-1.67(10H, m)<br>δ3.29-4.79(22H, m)<br>δ5.80-7.02(14H, m) |

TABLE 1-continued
| Compound | Structure | ¹H-NMR/IR(KBr) |
|---|---|---|
| 7 |  | δ0.96-1.25(30H, m)<br>δ3.29-4.65(78H, m)<br>δ5.80-6.43(18H, m) |
| 8 | 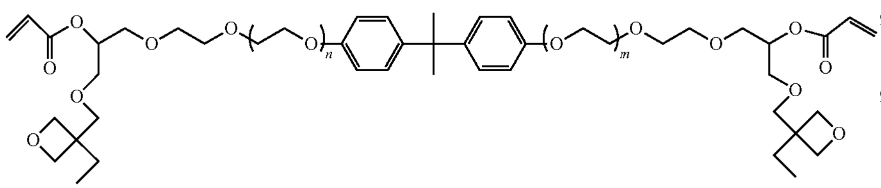 | 960.7 (m, Ar—H)<br>981(s, oxetane)<br>1630(s, C=C)<br>1720(s, C=O) |
| 9 | 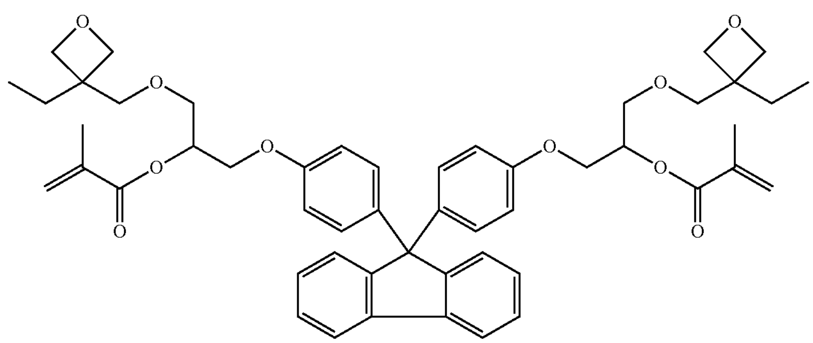 [SMILES: C=C(C)C(=O)OC(COCC1(CC)COC1)COc1ccc(C2(c3ccc(OCC(COCC4(CC)COC4)OC(=O)C(=C)C)cc3)c3ccccc3-c3ccccc32)cc1] | δ0.96-1.25(10H, m)<br>δ1.93(6H, m)<br>δ3.29-4.79(22H, m)<br>δ5.80-7.84(20H, m) |
| 10 | 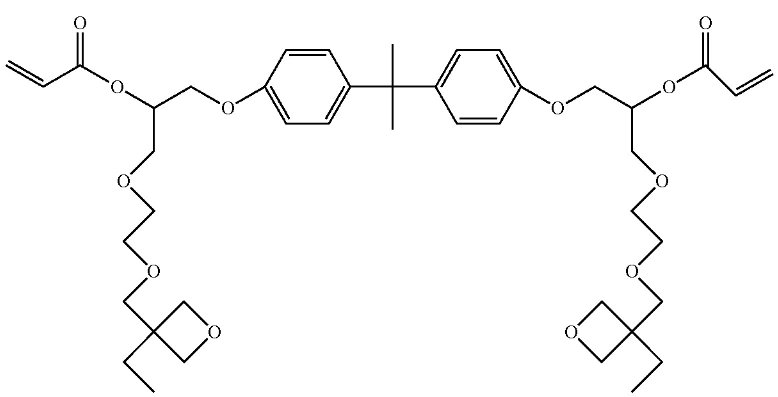 [SMILES: C=CC(=O)OC(COCCOCC1(CC)COC1)COc1ccc(C(C)(C)c2ccc(OCC(COCCOCC3(CC)COC3)OC(=O)C=C)cc2)cc1] | δ0.96-1.25(10H, m)<br>δ1.67(6H, s)<br>δ3.29-4.79(30H, m)<br>δ5.80-6.43(6H, m)<br>δ6.69-7.02(8H, d) |

TABLE 1-continued

| Compound | Structure | $^1$H-NMR/IR(KBr) |
|---|---|---|
| 11 | 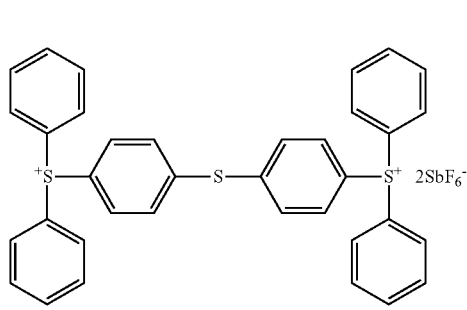 | δ0.96-1.25(10H, m)<br>δ1.93(6H, m)<br>δ3.29-4.79(30H, m)<br>δ5.80-6.15(4H, s)<br>δ6.65-7.84(16H, d) |

Test of Properties

1. Test of Curing Properties

By taking the compounds in the Examples described above as examples and adding a photoinitiator, curing properties of the disclosed photosensitive resin were tested.

During the test, pure cation systems or pure radical systems having the same functionality was used as comparative objects, comprising: a monofunctional cationic monomer, which was phenyl glycidyl ether (960, Hubei Jusheng Technology Co., Ltd.), a bifunctional cationic monomer, which was a bisphenol A type epoxy resin (E51, Jiangsu Sanmu Group), a trifunctional cationic monomer, which is diglycidyl 4,5-epoxycyclohexane-1,2-dicarboxylate (TDE-85, Tianjin Jindong Chemical Plant); a monofunctional radical monomer, which was β-hydroxyethyl acrylate (HEA, Sartomer), a bifunctional radical monomer, which was 1,6-hexanediol diacrylate (HDDA, Sartomer), a trifunctional radical monomer, which was trimethylolpropane triacrylate (TMPTA, Sartomer).

In the test, the cationic initiator was PAG-202, the radical initiator was 184, and their structures were as follows:

PAG202

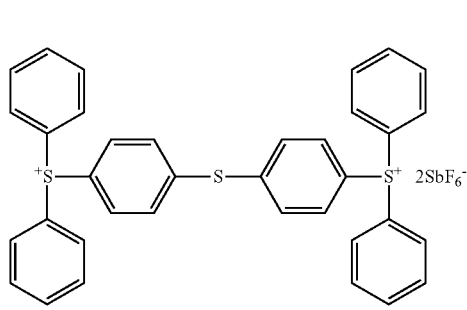

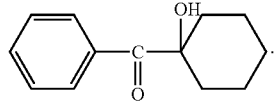

184

(1) Test 1—Cationic Monomer

Raw materials were selected with reference to the formulations as shown in Table 2. After evenly stirring in a dark room, a sample was taken on a PET film and coated with a 25# wire bar to form a coating film having a film thickness of about 25 μm. A PET film coated with a coating layer was placed in a track type exposure machine (RW-UV.70201 with a wavelength of 300-500 nm) and exposed. The energy received in a single exposure was 80 mj/cm$^2$. The lowest energy required for complete curing of each formulation was recorded.

The surface curing speed was evaluated with reference to the finger touch method in test standards for drying time of paint films, GB/T 1728-1979. That is, a coating layer was slightly touched with a finger and complete surface curing was indicated by a slippery and unsticky surface. A finger scratch method was used to measure the bottom curing speed. That is, a coating layer was slightly scratched with a fingernail and complete curing of the bottom layer was indicated by no phenomenon of peeling-off or exposed bottom.

Curing properties of the disclosed compounds and monomers having corresponding cationic functionalities were tested.

TABLE 2

|  | Formulation 1 | Formulation 2 | Formulation 3 | Formulation 4 | Formulation 5 | Formulation 6 |
|---|---|---|---|---|---|---|
| 960 | 6 g | — | — | — | — | — |
| E-51 | — | 6 g | — | — | — | — |
| TDE-85 | — | — | 6 g | — | — | — |
| Compound 1 | — | — | — | 6 g | — | — |
| Compound 4 | — | — | — | — | 6 g | — |
| Compound 5 | — | — | — | — | — | 6 g |
| PAG202 | 0.12 g | 0.12 g | 0.12 g | 0.06 g | 0.06 g | 0.06 g |
| 184 | — | — | — | 0.06 g | 0.06 g | 0.06 g |
| Exposure amount | 5 times | 4 times | 4 times | 2 times | 2 times | once |

(2) Test 2—Radical Monomer

Based on the formulations as shown in Table 3 and with reference to the methods as shown in Test 1, curing properties of the disclosed compounds and monomers having corresponding radical functionalities were tested.

TABLE 3

|  | Formulation 1 | Formulation 2 | Formulation 3 | Formulation 4 | Formulation 5 | Formulation 6 |
| --- | --- | --- | --- | --- | --- | --- |
| HEA | 6 g | — | — | — | — | — |
| HDDA | — | 6 g | — | — | — | — |
| TMPTA | — | — | 6 g | — | — | — |
| Compound 1 | — | — | — | 6 g | — | — |
| Compound 2 | — | — | — | — | 6 g | — |
| Compound 6 | — | — | — | — | — | 6 g |
| PAG202 | — | — | — | 0.06 g | 0.06 g | 0.06 g |
| 184 | 0.12 g | 0.12 g | 0.12 g | 0.06 g | 0.06 g | 0.06 g |
| Exposure amount | Not surface dried after 8 times | Not surface dried after 8 times | Not surface dried after 8 times | 2 times | once | 2 times |

As can be seen from the results in Table 2-3, when mixed with a radical-cation photoinitiator, the disclosed hybrid photosensitive resin had significant advantages in terms of curing efficiency. The energy required for complete curing was significantly lower than that of a monomer having the same cationic or radical functionality, and there was no problem of polymerization inhibition by oxygen. When having the same functionality, the disclosed photosensitive resin had a generally better curing speed.

2. Test of Properties after Film-Forming by Curing

By used in an exemplary photocurable composition, properties of the disclosed hybrid photosensitive resin after film-forming by curing were evaluated, which mainly included film hardness, adherence, flexibility, and heat resistance (in terms of glass transition temperature), wherein the disclosed photocurable composition was prepared according to the proportions as follows: the disclosed photosensitive resin (98 parts by mass); cationic initiator PAG-202 (1 part by mass); radical initiator 184 (1 part by mass).

The photocurable composition of Comparative Example 1 was prepared according to the proportion as follows: cation polymerizable monomer E-51 (98 parts by mass); cationic initiator PAG-202 (2 parts by mass).

The photocurable composition of Comparative Example 2 was prepared according to the proportion as follows: radical polymerizable monomer TMPTA (98 parts by mass); radical initiator 184 (2 parts by mass).

The photocurable composition of Comparative Example 3 was prepared according to the proportion as follows: photocurably polymerizable monomer, i.e., compound A (98 parts by mass); cationic initiator PAG-202 (1 part by mass); radical initiator 184 (1 part by mass).

Here, the compound A was a compound disclosed in JP2011168561A having a structure as follows:

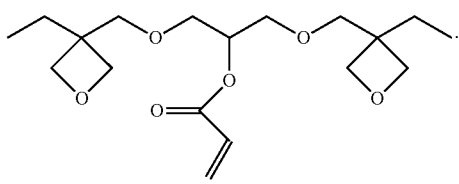 [SMILES: C=CC(=O)OC(COCC1(CC)COC1)COCC1(CC)COC1]

Formulated compositions were evenly stirred in a dark room, coated with 25# wire bars respectively on glass substrates to obtain coating layers having a thickness of about 25 µm. The coating layers were then placed in a track type exposure machine (RW-UV.70201 with a wavelength of 300-500 nm) and completely exposed 10 times, wherein each exposure was 80 mj/cm$^2$. A test was then performed after standing for 24h.

(1) Test of Pencil Hardness

Cured films of this disclosure and Comparative Examples were tested under conditions of a temperature of 23° C. and a relative humidity of 50%. The evaluation method for pencil hardness specified in GB/T 6739-2006 was used as a standard. A pencil was inserted into a test instrument, fixed with a clip, and maintained to be horizontal. The tip of the pencil was placed on the surface of a paint film, and was pushed by a distance of at least 7 mm at a speed of 1 mm/s toward a direction departing from yourself. If no scratch occurred, an experiment was repeated in an untested area by replacing with a pencil having a higher hardness, until a scratch having a length of at least 3 mm occurred. The hardness of the coating layer was represented by the hardness of hardest pencil which did not allow the occurrence of scratch on the coating layer.

(2) Test of Adherence

Cured films of this disclosure and Comparative Examples were tested under conditions of a temperature of 23° C. and a relative humidity of 50%. The evaluation method for paint film crosscut specified in GB/T 9286-1998 was used as a standard. A coating film was cut into one hundred grids. The tip of the cutter was required to scratch the substrate and to be sharp, and the angle formed between the tip of the cutter and the coating film was 45 degrees. Paint scraps were brushed off with a soft brush, a 3M adhesive tape was stuck onto the one hundred grids, and a force was applied to allow the adhesive tape to be firmly stuck onto the surface of the coating film and the crosscut parts. Within 2 min, one end of the 3M adhesive tape was held firmly to form an angle of 60 degrees, and the adhesive tape was steadily peeled off in 1 second. The evaluation was performed according to the criteria described below.

Grade 0: Cut edges were completely smooth and nothing fell off;

Grade 1: A few parts of the coating layer fell off at the intersections of cuts, but the influenced crosscut area could not be significantly greater than 5%;

Grade 2: Parts of the coating layer fell off at the intersections of cuts and/or along the edges of cuts, and the influenced crosscut area was significantly greater than 5% but could not be significantly greater than 15%;

Grade 3: The coating layer fell off partly or completely in the form of large fragments along the cut edges and/or fell off partly or completely on different parts of the grids, and the influenced crosscut area was significantly greater than 15% but could not be significantly greater than 35%;

Grade 4: The coating layer fell off in the form of large fragments along the cut edges and/or some grids fell off partly or completely, and the influenced crosscut area was significantly greater than 35% but could not be significantly greater than 65%;

Grade 5: The degree of falling-off exceeded Grade 4.

(3) Flexibility

Cured films of Examples and Comparative Examples were tested under conditions of a temperature of 23° C. and a relative humidity of 70%. On the basis of the test method of the flexibility of paint films in GB/T1731-93, the outside of a tin-plated steel plate coated with a cured coating layer was sequentially wound onto 10-, 5-, 4-, 3-, 2-, and 1-millimeter rod shafts along the length direction and bent for 2-3s. By observing with a magnifier, the flexibility of the photocured coating layer was represented by the diameter of the rod shaft having the smallest damage of the coating layer.

(4) Test of Heat Resistance

Glass transition temperatures of the disclosed cured films and Comparative Examples were tested by using a differential scanning calorimeter (PE DSC8000) under a test condition as follows: under a nitrogen atmosphere, the temperature was increased from −20° C. to 200° C. at a rate of 10° C./min and maintained at 200° C. for 1 min, then decreased from 200° C. to −20° C. at a rate of 10° C./min and maintained at −20° C. for 1 min, and increased from −20° C. to 200° C. at a rate of 10° C./min, so that the glass transition temperature Tg (° C.) was measured.

Results of tests and evaluations were summarized in Table 4.

TABLE 4

|  | Compound | Hardness | Adherence | Flexibility | Tg (° C.) |
|---|---|---|---|---|---|
| Disclosed Compounds | Compound 1 | 3H | Grade 0 | 1 | 85 |
|  | Compound 2 | 4H | Grade 1 | 2 | 105 |
|  | Compound 3 | 3H | Grade 0 | 1 | 89 |
|  | Compound 4 | 4H | Grade 0 | 1 | 96 |
|  | Compound 5 | 4H | Grade 1 | 2 | 102 |
|  | Compound 7 | 4H | Grade 1 | 3 | 132 |
|  | Compound 8 | 4H | Grade 0 | 1 | 108 |
|  | Compound 11 | 4H | Grade 0 | 2 | 122 |
| Comparative Example 1 | E51 | 2H | Grade 4 | 10 | 70 |
| Comparative Example 2 | TMPTA | 1H | Grade 5 | 5 | 45 |
| Comparative Example 3 | Compound A | 3H | Grade 2 | 5 | 80 |

As can be seen from Table 4, when used in a radical-cation curing system, the disclosed hybrid photosensitive resin can provide cured films with significantly higher hardness, better adherence, better flexibility, and better heat resistance, compared to E51 and TMPTA; and also exhibits better application properties in these four aspects, compared to the compound A of the same type.

In summary, the disclosed hybrid photosensitive resin compound combines advantages of cation curing and radical curing, has high curing efficiency as well as excellent hardness, adherence, flexibility, and heat resistance of cured films, and has a simple synthesis method and many types. This provides a good promotional effect on generalization and application in the field of photocuring.

Those described above are merely preferred Examples of this invention, and are not intended to limit this invention. With respect to the person skilled in the art, there may be various modifications and variations of this invention. All of modifications, equivalent replacements, improvements, and the like, which are within the spirit and the principle of this invention, should be encompassed in the scope protected by this invention.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. A hybrid photosensitive resin, wherein the hybrid photosensitive resin has a structure represented by general formula (I):

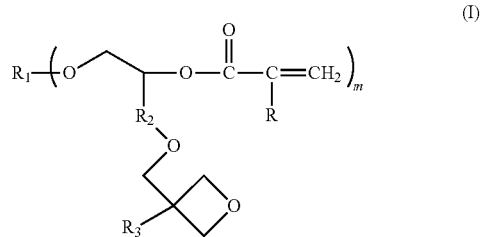

wherein $R_1$ represents a $C_1$-$C_{40}$ linear m-valent alkyl group, a branched m-valent alkyl group, a $C_2$-$C_{20}$ m-valent alkenyl group, or a $C_6$-$C_{40}$ m-valent aryl group, wherein —$CH_2$— can be substituted with an oxygen atom, —NH—, or a 1,4-phenylene group, provided that two —O—'s are not directly connected; wherein, one or more hydrogen atoms in these groups can be each independently substituted with a group selected from an alkyl group, a halogen, and a nitro group;

wherein $R_2$ represents a $C_1$-$C_{20}$ linear alkylene group or a $C_1$-$C_{20}$ branched alkylene group, wherein —$CH_2$— in the main chain can be substituted with an oxygen atom, provided that two —O—'s are not directly connected, and optionally, one or more hydrogen atoms in the group can be each independently substituted with a group selected from an alkyl group, a halogen, and a nitro group;

wherein $R_3$ represents hydrogen, a halogen, a nitro group, a $C_1$-$C_{20}$ linear alkyl group, a $C_1$-$C_{20}$ branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_2$-$C_{10}$ alkenyl group, or a $C_6$-$C_{20}$ aryl group, and wherein, one or more hydrogen atoms in these groups can be each independently substituted with a group selected from an alkyl group, a halogen, and a nitro group;

wherein R represents hydrogen or a methyl group; and wherein m represents an integer of 1-8.

2. The hybrid photosensitive resin according to claim 1, wherein $R_1$ represents a $C_1$-$C_{40}$ linear m-valent alkyl group, a $C_1$-$C_{40}$ branched m-valent alkyl group, a $C_2$-$C_{10}$ linear m-valent alkenyl group, a $C_2$-$C_{10}$ branched m-valent alkenyl group, or a $C_6$-$C_{30}$ m-valent aryl group, wherein —$CH_2$— can be substituted with an oxygen atom, —NH—, or a 1,4-phenylene group, provided that two —O—'s are not directly connected; and wherein, one or more hydrogen atoms in these groups can be each independently substituted with a group selected from an alkyl group, a halogen, and a nitro group.

3. The hybrid photosensitive resin according to claim 1, wherein $R_1$ is selected from the following structures: a $C_1$-$C_{12}$ linear or branched 1-to-4-valent alkyl group,

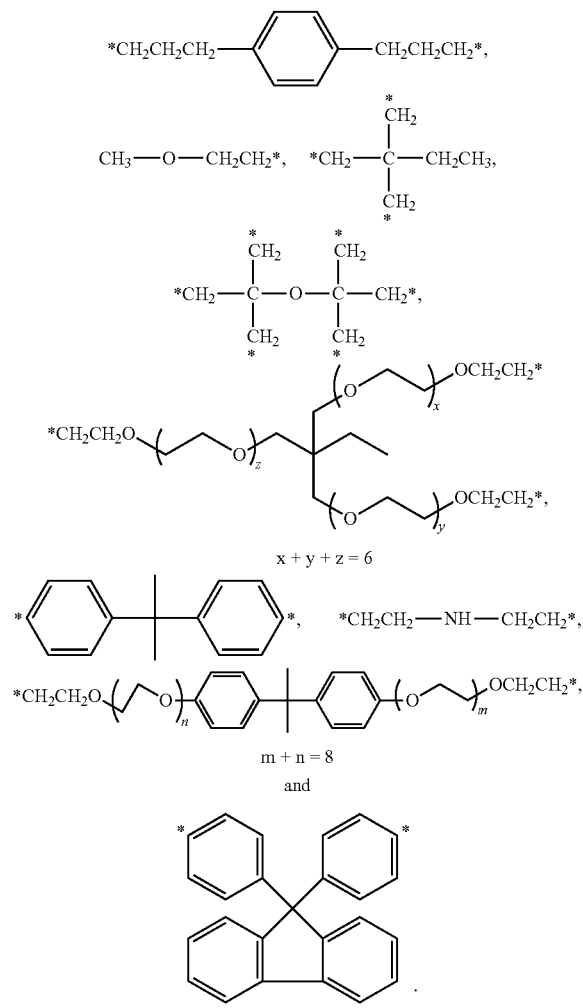

4. The hybrid photosensitive resin according to claim 1, wherein $R_2$ represents a $C_1$-$C_{10}$ linear alkylene group, a $C_1$-$C_{10}$ branched alkylene group, wherein —CH$_2$— in the main chain can be substituted with an oxygen atom, provided that two —O—'s are not directly connected.

5. The hybrid photosensitive resin according to claim 1, wherein $R_3$ represents hydrogen, a $C_1$-$C_{10}$ linear alkyl group, a $C_1$-$C_{10}$ branched alkyl group, a $C_3$-$C_{10}$ cycloalkyl group, a $C_4$-$C_{10}$ cycloalkylalkyl group, a $C_4$-$C_{10}$ alkylcycloalkyl group, a $C_2$-$C_8$ alkenyl group, or a phenyl group.

6. The hybrid photosensitive resin according to claim 1, wherein m is an integer of 1-6.

7. A preparation method of the hybrid photosensitive resin of claim 1, wherein a hydroxy-containing compound represented by $R_1$—(OH)$_m$ and an oxetanyl-containing compound represented by

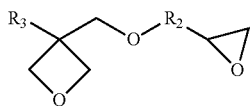

are used as starting materials, and the preparation method comprises the steps of:

(a) a ring opening reaction, wherein said hydroxy-containing compound is reacted with said oxetanyl-containing compound in the presence of a first catalyst to obtain an intermediate; and a reaction formula thereof is as follows:

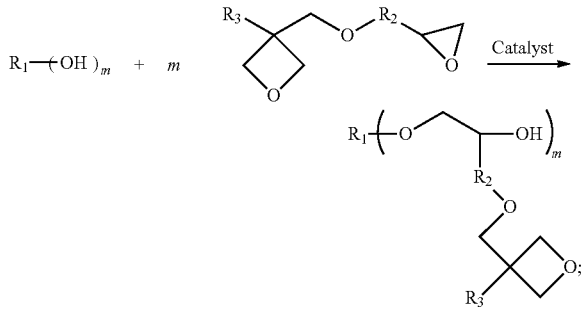

(b) an esterification/transesterfication reaction, wherein the intermediate is reacted with (meth)acrylic acid or (meth)acrylate in the presence of a second catalyst to obtain a product;

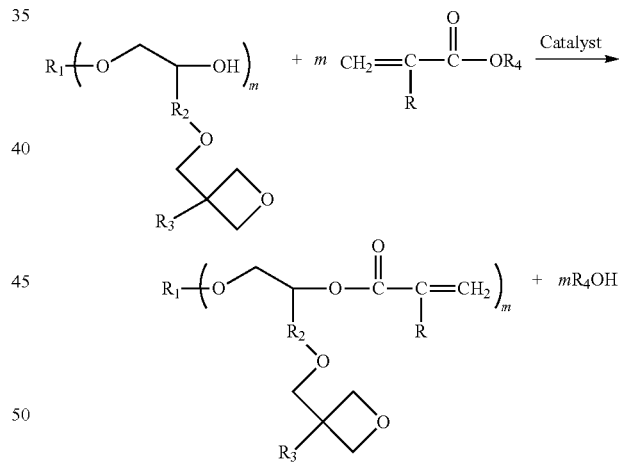

wherein $R_4$ represents hydrogen or a $C_1$-$C_4$ alkyl group.

8. The preparation method according to claim 7, wherein said first catalyst is selected from one or a combination of two or more of an alkali metal hydroxide, an alkali metal salt of an alcohol, an alkali metal carbonate, an alkali metal bicarbonate, an alkyl metal lithium compound, and a lithium amide compound.

9. The preparation method according to claim 7, wherein the intermediate is subjected to esterification reaction with (meth)acrylic acid or transesterfication reaction with (meth) acrylate to obtain the product; said second catalyst used in the esterification reaction is an inorganic acid or an organic acid, and the catalyst used in the transesterfication reaction is a titanate-based compound.

10. The hybrid photosensitive resin according to claim 1, wherein $R_2$ represents a $C_1$-$C_6$ linear alkylene group or a $C_1$-$C_6$ branched alkylene group, wherein —$CH_2$— in the main chain can be substituted with an oxygen atom, provided that two —O—'s are not directly connected.

11. The hybrid photosensitive resin according to claim 1, wherein $R_3$ represents a $C_1$-$C_4$ linear alkyl group, a $C_1$-$C_4$ branched alkyl group, or a $C_4$-$C_8$ cycloalkylalkyl group.

12. The hybrid photosensitive resin according to claim 1, wherein m is an integer of 1-4.

* * * * *